United States Patent
Pilly et al.

(10) Patent No.: US 10,744,321 B2
(45) Date of Patent: Aug. 18, 2020

(54) TRANSCRANIAL CURRENT STIMULATION SYSTEM AND VIRTUAL REALITY FOR TREATMENT OF PTSD OR FEARS

(71) Applicant: HRL Laboratories, LLC, Malibu, CA (US)

(72) Inventors: Praveen K. Pilly, West Hills, CA (US); Michael D. Howard, Westlake Village, CA (US)

(73) Assignee: HRL Laboratories, LLC, Malibu, CA (US)

( * ) Notice: Subject to any disclaimer, the term of this patent is extended or adjusted under 35 U.S.C. 154(b) by 248 days.

(21) Appl. No.: 15/874,866

(22) Filed: Jan. 18, 2018

(65) Prior Publication Data

US 2018/0154148 A1    Jun. 7, 2018

Related U.S. Application Data

(63) Continuation-in-part of application No. 15/332,787, filed on Oct. 24, 2016, now Pat. No. 10,307,592.
(Continued)

(51) Int. Cl.
*A61N 1/04* (2006.01)
*A61N 1/36* (2006.01)
(Continued)

(52) U.S. Cl.
CPC ........ *A61N 1/36025* (2013.01); *A61B 5/0476* (2013.01); *A61B 5/4812* (2013.01);
(Continued)

(58) Field of Classification Search
CPC .............. A61N 1/36025; A61N 1/0456; A61N 1/0476; A61N 1/36031; A61N 1/20;
(Continued)

(56) References Cited

U.S. PATENT DOCUMENTS 6,012,926 A    1/2000  Hodges et al.
6,751,505 B1   6/2004  Van Den Honert
(Continued)

FOREIGN PATENT DOCUMENTS

EP        2409641 A1    1/2012
WO    WO 2016-182947 A1    11/2016

OTHER PUBLICATIONS

Bikson, M., Bestmann, S., & Edwards, D. (2013). Neuroscience: transcranial devices are not playthings. Nature, 501(7466), pp. 167-167.
(Continued)

*Primary Examiner* — Rex R Holmes
(74) *Attorney, Agent, or Firm* — Tope-McKay & Associates

(57) ABSTRACT

Described is a system for treating traumatic memories. During a wake stage, a virtual environment is displayed to a subject. A traumatic episode that may be similar to a traumatic memory of the subject is displayed to the user in the virtual environment in a benign setting. A transcranial current stimulation (tCS) controller applies a pattern of transcranial direct current stimulation (tDCS) to the subject during the traumatic episode, such that the traumatic memory in a benign setting is associated with the pattern of tDCS. During a sleep stage, if slow-wave sleep in the subject is detected via electroencephalogram (EEG) recordings, then in a first time period, the tCS controller may a transcranial alternating current stimulation (tACS) to the subject followed by a second time period without stimulation. In a third time period, the tCS controller may apply the pattern of tDCS to the subject. The sleep stage may be repeated until a desired weakening of the traumatic memory is reached.

21 Claims, 5 Drawing Sheets

Related U.S. Application Data

(60) Provisional application No. 62/245,730, filed on Oct. 23, 2015, provisional application No. 62/516,350, filed on Jun. 7, 2017, provisional application No. 62/478,538, filed on Mar. 29, 2017.

(51) Int. Cl.

| | |
|---|---|
| *A61N 1/20* | (2006.01) |
| *A61B 5/00* | (2006.01) |
| *G06T 11/60* | (2006.01) |
| *A61B 5/0476* | (2006.01) |
| *A61M 21/00* | (2006.01) |
| *A61B 5/0478* | (2006.01) |
| *A61B 5/048* | (2006.01) |

(52) U.S. Cl.
CPC .......... *A61B 5/4836* (2013.01); *A61B 5/6814* (2013.01); *A61M 21/00* (2013.01); *A61N 1/20* (2013.01); *A61N 1/36031* (2017.08); *G06T 11/60* (2013.01); *A61B 5/048* (2013.01); *A61B 5/0478* (2013.01); *A61M 2021/0055* (2013.01); *A61M 2205/52* (2013.01); *A61M 2230/10* (2013.01); *A61N 1/0456* (2013.01); *A61N 1/0476* (2013.01); *G06T 2210/41* (2013.01)

(58) Field of Classification Search
CPC .............. A61M 21/00; A61M 2230/10; A61M 2205/52; A61M 2021/0055; A61B 5/6814; A61B 5/0476; A61B 5/4836; A61B 5/4812; A61B 5/048; A61B 5/0478; G06T 2210/41; G06T 11/60
See application file for complete search history.

(56) References Cited

U.S. PATENT DOCUMENTS

| | | | |
|---|---|---|---|
| 9,089,703 B2 | 7/2015 | Rodriguez et al. | |
| 2003/0225340 A1 | 12/2003 | Collura | |
| 2007/0213786 A1 | 9/2007 | Sackellares et al. | |
| 2012/0265261 A1 | 10/2012 | Bikson et al. | |
| 2014/0275926 A1 | 9/2014 | Scott et al. | |
| 2018/0221644 A1 | 8/2018 | Grill | |
| 2019/0329063 A1* | 10/2019 | Hendler | A61B 5/486 |

OTHER PUBLICATIONS

Brunoni, A. R., Nitsche, M. A., Bolognini, N., Bikson, M., Wagner, T., Merabet, L., . . . & Ferrucci, R. (2012). Clinical research with transcranial direct current stimulation (tDCS): challenges and future directions. Brain stimulation, 5(3), pp. 175-195.

Choe, J., Coffman, B. A., Bergstedt, D. T., Ziegler, M. D., & Phillips, M. E. (2016). Transcranial direct current stimulation modulates neuronal activity and learning in pilot training. Frontiers in human neuroscience, 10, pp. 1-25.

Schultz DM, Webster L, Kosek P, et al. Sensor-driven position-adaptive spinal cord stimulation for chronic pain. Pain Physician 2012;15: pp. 1-12.

Jacobson, L., Koslowsky, M., & Lavidor, M. (2012). tDCS polarity effects in motor and cognitive domains: a meta-analytical review. Experimental brain research, 216(1), pp. 1-10.

Osorio I, Frei MG, Sunderam S, et al. Automated seizure abatement in humans using electrical stimulation. Ann Neurol 2005;57: pp. 258-268.

Berényi, A., Belluscio, M., Mao, D., & Buzsáki, G. (2012). Closed-loop control of epilepsy by transcranial electrical stimulation. Science, 337(6095), pp. 735-737.

Tergau, F., Naumann, U., Paulus, W., & Steinhoff, B. J. (1999). Low-frequency repetitive transcranial magnetic stimulation improves intractable epilepsy. The Lancet, 353(9171), p. 2209.

Nitsche, M. A., Cohen, L. G., Wassermann, E. M., Priori, A., Lang, N., Antal, A., . . . & Pascual-Leone, A. (2008). Transcranial direct current stimulation: state of the art 2008. Brain stimulation, 1(3), pp. 206-223.

Ferrucci, R., Mameli, F., Guidi, I., Mrakic-Sposta, S., Vergari, M., Marceglia, S. E. E. A., . . . & Priori, A. (2008). Transcranial direct current stimulation improves recognition memory in Alzheimer disease. Neurology, 71(7), pp. 493-498.

Clark, V. P., Coffman, B. A., Mayer, A. R., Weisend, M. P., Lane, T. D., Calhoun, V. D., . . . & Wassermann, E. M. (2012). TDCS guided using fMRI significantly accelerates learning to identify concealed objects. Neuroimage, 59(1), pp. 117-128.

Gálvez-García, G., Albayay, J., Rehbein, L., & Tornay, F. (2017). Mitigating Simulator Adaptation Syndrome by means of tactile stimulation. Applied Ergonomics, 58, pp. 13-17.

Ngo, H. V. V., Miedema, A., Faude, I., Martinetz, T., Mölle, M., & Born, J. (2015). Driving Sleep Slow Oscillations by Auditory Closed-Loop Stimulation—A Self-Limiting Process. The Journal of Neuroscience, 35(17), pp. 6630-6638.

Cox, R., Korjoukov, I., de Boer, M., & Talamini, L. M. (2014). Sound asleep: processing and retention of slow oscillation phase-targeted stimuli. PloS one, 9(7), e101567, pp. 1-12.

Santostasi, G., Malkani, R., Riedner, B., Bellesi, M., Tononi, G., Paller, K. A., & Zee, P. C. (2016). Phase-locked loop for precisely timed acoustic stimulation during sleep. Journal of neuroscience methods, 259, pp. 101-114.

Van Elmpt WJ, Nijsen TM, Griep PA, et al. A model of heart rate changes to detect seizures in severe epilepsy. Seizure 2006;15: pp. 366-375.

Schade CM, Schultz DM, Tamayo N, et al. Automatic adaptation of neurostimulation therapy in response to changes in patient position: results of the Posture Responsive Spinal Cord Stimulation (PRS) Research Study. Pain Physician 2011;14: pp. 407-417.

Little S, Pogosyan A, Neal S, et al. Adaptive deep brain stimulation in advanced Parkinson disease. Ann Neurol 2013;74: pp. 449-457.

Marshall L, Helgadóttir H, Mölle M, Born J. Boosting slow oscillations during sleep potentiates memory. Nature. 2006; 444(7119): pp. 610-613.

Rudoy JD, Voss JL, Westerberg CE, Paller KA. Strengthening Individual Memories by Reactivating Them During Sleep. Science. Nov. 20, 2009;326(5956): pp. 1079-1079.

Diekelmann S, Biggel S, Rasch B, Born J. Offline consolidation of memory varies with time in slow wave sleep and can be accelerated by cuing memory reactivations. Neurobiol Learn Mem. Sep. 2012; 98(2): pp. 103-111.

Rasch BH, Born J, Gais S. Combined blockade of cholinergic receptors shifts the brain from stimulus encoding to memory consolidation. J Cogn Neurosci. May 2006; 18(5): pp. 793-802.

Gais S, Born J. Low acetylcholine during slow-wave sleep is critical for declarative memory consolidation. Proc Natl Acad Sci U S A. Feb. 17, 2004; 101(7): pp. 2140-2144.

Rasch B, Buchel C, Gais S, Born J. Odor cues during slow-wave sleep prompt declarative memory consolidation. Science. 2007; 315(5817): pp. 1426-1429.

Kirov R, Weiss C, Siebner HR, Born J, Marshall L. Slow oscillation electrical brain stimulation during waking promotes EEG theta activity and memory encoding. Proc. Natl. Acad. Sci. 2009;106: pp. 15460-15465.

Jutras MJ, Fries P, Buffalo EA. Oscillatory activity in the monkey hippocampus during visual exploration and memory formation. Proc Natl Acad Sci. Aug. 6, 2013; 110(32): pp. 13144-13149.

Brincat SL, Miller EK. Frequency-specific hippocampal-prefrontal interactions during associative learning. Nat Neurosci. Apr. 2015; 18(4): pp. 576-581.

McNamara CG, Tejero-Cantero A, Trouche S, Campo-Urriza N, Dupret D. Dopaminergic neurons promote hippocampal reactivation and spatial memory persistence. Nat Neurosci. 2014 12//print; 17(12): pp. 1658-1660.

Ji D, Wilson MA. Coordinated memory replay in the visual cortex and hippocampus during sleep. Nat Neurosci. 2007; 10(1): pp. 100-107.

(56) References Cited

OTHER PUBLICATIONS

Kali S, Dayan P. Off-line replay maintains declarative memories in a model of hippocampal-neocortical interactions. Nat Neurosci. 2004; 7(3): pp. 286-294.

Rolls ET. Hippocampo-cortical and cortico-cortical backprojections. Hippocampus. 2000; 10: pp. 380-388.

Creutzfeldt OD, Fromm GH, Kapp H. Influence of transcortical d-c currents on cortical neuronal activity. Exp Neurol. Jun. 1962; 5: pp. 436-452.

Sederberg PB, Kahana MJ, Howard MW, Donner EJ, Madsen JR. Theta and gamma oscillations during encoding predict subsequent recall. J Neurosci Off J Soc Neurosci. Nov. 26, 2006; 23(34): pp. 10809-10814.

Osipova D, Takashima A, Oostenveld R, Fernandez G, Maris E, Jensen O. Theta and gamma oscillations predict encoding and retrieval of declarative memory. J Neurosci. 2006; 26(28): pp. 7523-7531.

Fröhlich F, McCormick DA. Endogenous electric fields may guide neocortical network activity. Neuron. Jul. 15, 2010; 67(1): pp. 129-143.

Ngo, H. V. V., Martinetz, T., Born, J., & Mölle, M. (2013). Auditory closed-loop stimulation of the sleep slow oscillation enhances memory. Neuron, 78(3), pp. 545-553.

Foa EB. Social anxiety disorder treatments: psychosocial therapies. J. Clin. Psychiatry. 2006;67 Suppl 12: pp. 27-30.

Bustos SG, Maldonado H, Molina VA. Midazolam disrupts fear memory reconsolidation. Neuroscience. 2006;139: pp. 831-842.

Chan JCK, LaPaglia JA. Impairing existing declarative memory in humans by disrupting reconsolidation. Proc. Natl. Acad. Sci. 2013;110: pp. 9309-9313.

Brunet A, Orr SP, Tremblay J, Robertson K, Nader K, Pitman RK. Effect of post-retrieval propranolol on psychophysiologic responding during subsequent script-driven traumatic imagery in post-traumatic stress disorder. J. Psychiatr. Res. 2008;42: pp. 503-506.

Marshall, L, Helgadóttir, H, Mölle, M, Born, J. Boosting Slow Oscillations During Sleep Potentiates Memory. Nature. 2006; 444, pp. 610-613.

Cox R, Korjoukov I, de Boer M, Talamini LM. Sound Asleep: Processing and Retention of Slow Oscillation Phase-Targeted Stimuli. PLoS ONE. 2014; 9(7), pp. 1-12.

Weathers, FW, Blake, DD, Schnurr, PP, Kaloupek, DG, Marx, BP, & Keane, TM. The Clinician-Administered PTSD Scale for DSM-5 (CAPS-5). 2013, pp. 1-4.

Notification of Transmittal of International Search Report and the Written Opinion of the International Searching Authority for PCT/US2018/014294; dated May 3, 2018.

International Search Report of the International Searching Authority for PCT/US2018/014294; dated May 3, 2018.

Written Opinion of the International Searching Authority for PCT/US2018/014294; dated May 3, 2018.

Novakovic, V., et. al., "Brain stimulation in post traumatic stress disorder," European Journal of Psychotraumatology, 2011, vol. 2, Article No. 5609, pp. 1-12.

Martin, M., F., et al., "Neuromodulation approaches for the treatment of post-traumatic stress disorder: stimulating the brain following exposure-based therapy," Current Behavioral Neuroscience Reports, 2015, vol. 2, Issue 2, pp. 67-71.

Office Action 1 for U.S. Appl. No. 15/947,733, dated Feb. 1, 2019.

Response to Office Action 1 for U.S. Appl. No. 15/947,733, dated Apr. 16, 2019.

Notice of Allowance for U.S. Appl. No. 15/947,733, dated May 8, 2019.

Office Action 1 for U.S. Appl. No. 15/332,787, dated Sep. 18, 2018.

Response to Office Action 1 for U.S. Appl. No. 15/332,787, dated Nov. 6, 2018.

Notice of Allowance for U.S. Appl. No. 15/332,787, dated Jan. 17, 2019.

Notification of and the International Preliminary Report on Patentability Chapter I for PCT/US2018/014294; dated Oct. 10, 2019.

Notification of the International Preliminary Report on Patentability Chapter I for PCT/US2018/026614; dated Nov. 14, 2019.

The International Preliminary Report on Patentability Chapter I for PCT/US2018/026614; dated Nov. 14, 2019.

Notification of Transmittal of International Search Report and the Written Opinion of the International Searching Authority for PCT/US2018/026614; dated Aug. 27, 2018.

International Search Report of the International Searching Authority for PCT/US2018/026614; dated Aug. 27, 2018.

Written Opinion of the International Searching Authority for PCT/US2018/026614; dated Aug. 27, 2018.

* cited by examiner

TRANSCRANIAL CURRENT STIMULATION SYSTEM AND VIRTUAL REALITY FOR TREATMENT OF PTSD OR FEARS

CROSS-REFERENCE TO RELATED APPLICATIONS

This is a Continuation-in-Part application of U.S. Non-Provisional Application Ser. No. 15/332,787, filed in the United States on Oct. 24, 2016, entitled, "Method and System to Accelerate Consolidation of Specific Memories Using Transcranial Stimulation," which is a Non-Provisional patent application of 62/245,730, filed in the United States on Oct. 23, 2015, entitled, "Method and System to Accelerate Consolidation of Specific Memories Using Transcranial Stimulation," the entirety of which are hereby incorporated by reference.

The present application is ALSO a Non-Provisional patent application of U.S. Provisional Application No. 62/516,350, filed in the United States on Jun. 7, 2017, entitled, "A Method for Low Latency Automated Closed-Loop Synchronization of Neurostimulation Interventions to Neurophysiological Activity," the entirety of which is hereby incorporated by reference.

The present application is ALSO a Non-Provisional patent application of U.S. Provisional Application No. 62/478,538, filed in the United States on Mar. 29, 2017, entitled, "Transcranial Current Stimulation System and Virtual Reality for Treatment of PTSD and Irrational Fears," the entirety of which is hereby incorporated by reference.

GOVERNMENT LICENSE RIGHTS

This invention was made with government support under U.S. Government Contract Number W911NF-16-C-0018. The government may have certain rights in the invention.

BACKGROUND OF INVENTION (1) Field of Invention

The present invention relates to a system for treatment of traumatic memories and, more particularly, to a system for treatment of traumatic memories using a combination of transcranial current stimulation and virtual reality.

(2) Description of Related Art

Traumatic memories are intense, stressful, and emotionally paralyzing. The reconsolidation hypothesis states that when a consolidated memory is recalled, it becomes unstable and susceptible to modification for a discrete period of time, gradually becoming stable again. The most common method for treatment of post-traumatic stress disorder (PTSD) is aversion therapy under the guidance of a psychologist or psychiatrist, in order to associate more benign, safe feelings with the stressful memory. However, this process is inefficient; it can take years of therapy to overcome the painful memory, since the intense emotion of the initial experience causes it to be strongly encoded.

Prior art methods to impair existing declarative memories in humans by disrupting reconsolidation either use a behavioral re-conditioning paradigm during waking (see Literature Reference No. 4 of the List of Incorporated Literature References) or employ drugs that inhibit protein synthesis during or following the experience of a traumatic memory (see Literature Reference No. 5). Often, medication such as Prozac or Zoloft is prescribed to PTSD sufferers, but these antidepressants do not treat the causes, only the symptoms, and have the potential for psychological dependence and addiction. Midazolam specifically disrupts reconsolidation (see Literature Reference No. 2), but it is a powerful sedative, also used as a lethal injection drug, and can be dangerous.

Furthermore, prior art psychological trauma counseling is a very slow process that can take years. As an alternative to traditional "talk therapy", Virtual Reality is recently being explored to increase the power of a recalled traumatic episode. One example is the BRAVEMIND program being funded by ARL for military PTSD treatment. Another example is used to treat a fear of flying. However, none of these methods use cued recall during sleep to consolidate the treatment into long-term memory.

Thus, a continuing need exists for a system that employs high-definition transcranial current stimulation during both waking and sleep to proactively disrupt the cycle of reconsolidation of a traumatic memory and to promote consolidation of a new, more benign association, to weaken the effect of the trauma electrically.

SUMMARY OF INVENTION

The present invention relates to a system for treatment of traumatic memories and, more particularly, to a system for treatment of traumatic memories using a combination of transcranial current stimulation and virtual reality. The system comprises one or more processors and a non-transitory computer-readable medium having executable instructions encoded thereon such that when executed, the one or more processors perform multiple operations. During a wake stage, the system causing a virtual environment to be displayed via a virtual reality system in a benign setting. A traumatic episode is displayed in the virtual environment via the virtual reality system, wherein the traumatic episode is created to include painful aspects of a traumatic memory. Using a transcranial current stimulation (tCS) controller, a pattern of transcranial direct current stimulation (tDCS) is applied while the traumatic episode is being displayed via the virtual reality system to associate the traumatic memory with the pattern of tDCS given in the benign setting.

In another aspect, during a sleep stage, if a period of slow-wave sleep is detected via electroencephalogram (EEG) recordings, then the system causes the tCS controller to apply a transcranial alternating current stimulation (tACS) to the prefrontal cortex of the subject.

In another aspect, the virtual environment is gradually altered to be similar to an environment in which the subject experienced the traumatic memory.

In another aspect, the pattern of tDCS is a Spatial-Temporal Amplitude Modulated Pattern (STAMP).

In another aspect, the duration of the tDCS application is varied based on the traumatic memory.

In another aspect, the period of slow-wave sleep comprises a slow-wave oscillation, and wherein the system, using the tCS controller, applies the pattern of tDCS for at least a portion of the slow-wave oscillation.

In another aspect, the slow-wave oscillation comprises a plurality of UP phases, and the system, using the tCS controller, applies the pattern of tDCS to a percentage of the plurality of UP phases.

In another aspect, the virtual environment is altered in a series of sessions to gradually increase the level of discomfort of a subject.

In another aspect, following a duration of application of the tACS to the prefrontal cortex of the subject, a duration of no stimulation occurs, wherein the duration of no stimulation is shorter than the duration of application of the tACS, and wherein following the duration of no stimulation, the system causes the tCS controller to apply the pattern of tDCS to the subject to weaken the traumatic memory.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
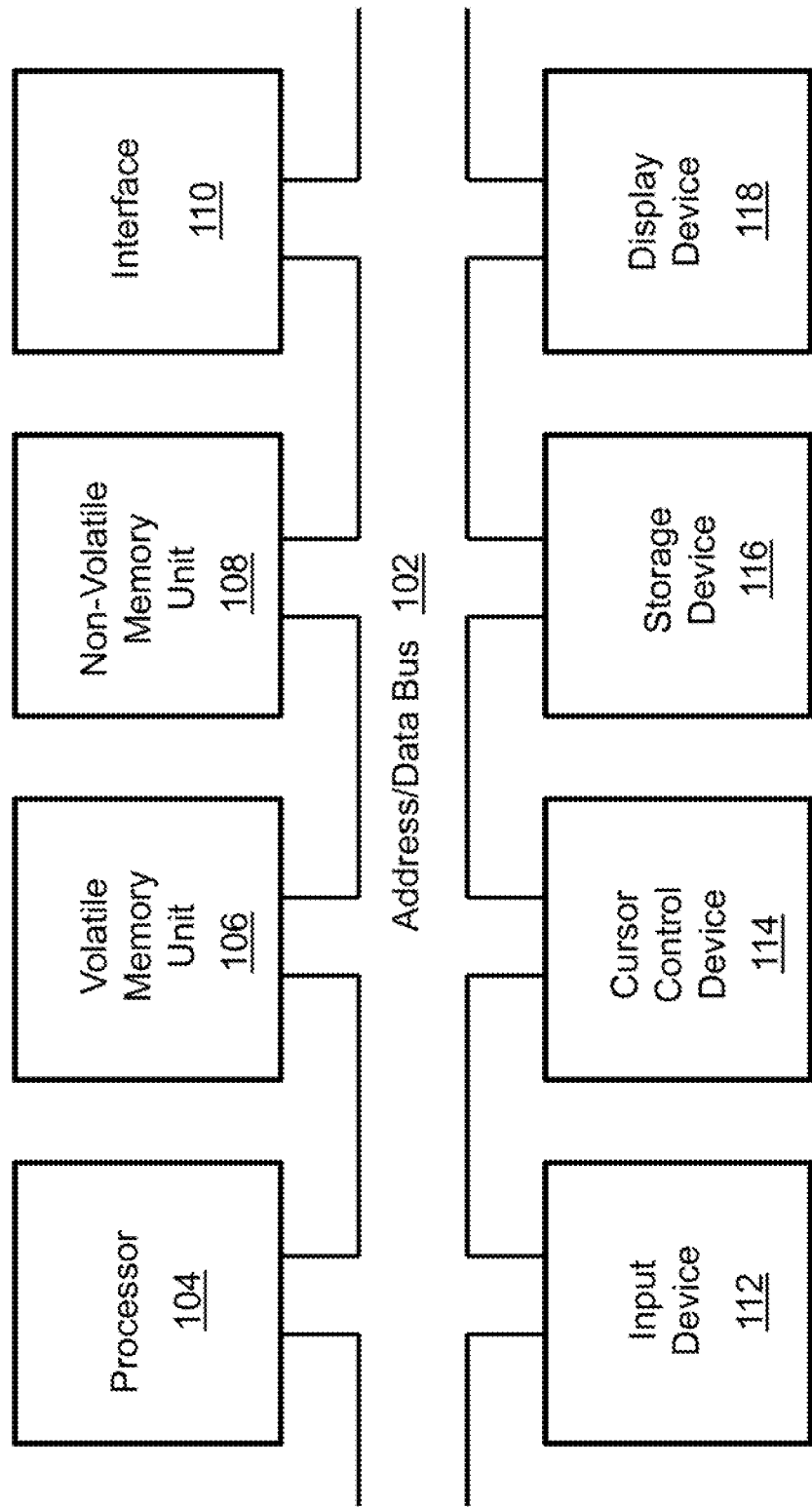
FIG. 1 is a block diagram depicting the components of a system for treatment of traumatic memories according to some embodiments of the present disclosure.

The present invention relates to a system for treatment of traumatic memories and, more particularly, to a system for treatment of traumatic memories using a combination of transcranial current stimulation and virtual reality. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) List of Incorporated Literature References

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number, as follows:

1. Foe E B. Social Anxiety Disorder Treatments: Psychosocial Therapies. J. Clin. Psychiatry. 2006; 67 Suppl 12:27-30.
2. Bustos S G, Maldonado H, Molina V A. Midazolam Disrupts Fear Memory Reconsolidation. Neuroscience. 2006; 139: 831-42.
3. Bikson M, Datta A, Parra L C, Dmochowski J, Su Y. Neurocranial Electrostimulation Models, Systems, Devices, and Methods. July.
4. Chan J C K, LaPaglia J A. Impairing Existing Declarative Memory in Humans by Disrupting Reconsolidation. Proc. Nati. Acad. Sci. 2013; 110: 9309-13.
5. Brunet A, Orr S P, Tremblay J, Robertson K, Nader K, Pitman R K. Effect of Post-Retrieval Propranol on Psychophysiologic Responding During Subsequent Script-Driven Traumatic imagery in Post-Traumatic Stress Disorder. J. Psychiatr. Res. 2008; 42: 503-6.
6. Marshall, L, Helgadóttir, H, Mölle, M, Born, J. Boosting Slow Oscillations During Sleep Potentiates Memory. Nature. 2006; 444, 610-613.
7. Cox R, Korjoukov I, de Boer M, Talamini L M. Sound Asleep: Processing and Retention of Slow Oscillation Phase-Targeted Stimuli. PLoS ONE. 2014; 9(7).
8. Weathers, F W, Blake, D, Schnurr, P P, Kaloupek, D G, Marx, B P, & Keane, $T_M$. The Clinician-Administered PTSD Scale for DSM-5 (CAPS-5). 2013.

(2) Principal Aspects

Various embodiments of the invention include three "principal" aspects. The first is a system for treatment of traumatic memories. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
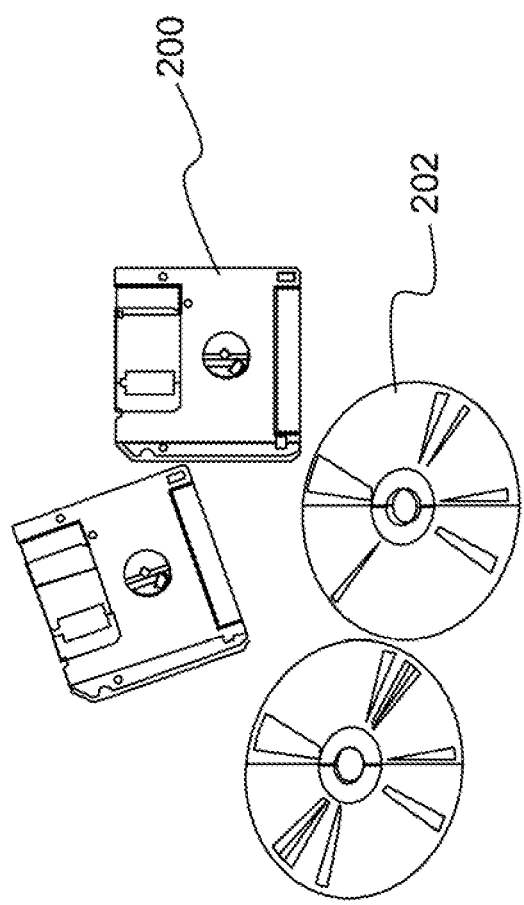
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of Various Embodiments

Traumatic memories are intense, stressful, and emotionally paralyzing. The reconsolidation hypothesis states that when a consolidated memory is recalled, it becomes unstable and susceptible to modification for a discrete period of time, gradually becoming stable again. The most common method for treatment of PTSD is aversion therapy under the guidance of a psychologist or psychiatrist, in order to associate more benign (i.e., gentle, not harmful), safe feelings with the stressful memory. However, this process is inefficient; it can take years of therapy to overcome the painful memory, since the intense emotion of the initial experience causes it to be strongly encoded.

The system described herein will make these therapy sessions with the professional much more effective, achieving the goals of therapy much faster. The system consists of two stages. The first stage is to employ virtual reality to evoke the painful memory, including painful aspects of the memory, under safe and controlled conditions (e.g., a benign setting). Safe and controlled conditions may simply involve being in a home or office.

The benign setting is key, because the subject can experience the traumatic memory with less fear and stress. This is the basis of aversion therapy. This, in itself, is not new, but it increases the efficacy of the second stage. The second stage of the system is to apply a weak, unique pattern of electrical stimulation to the scalp during one or more of these aversion therapy sessions, and then use this same pattern as a cue during sleep to promote reactivation of the new benign association during sleep, consolidating it much faster than normal.

Figures 3A, 3B:
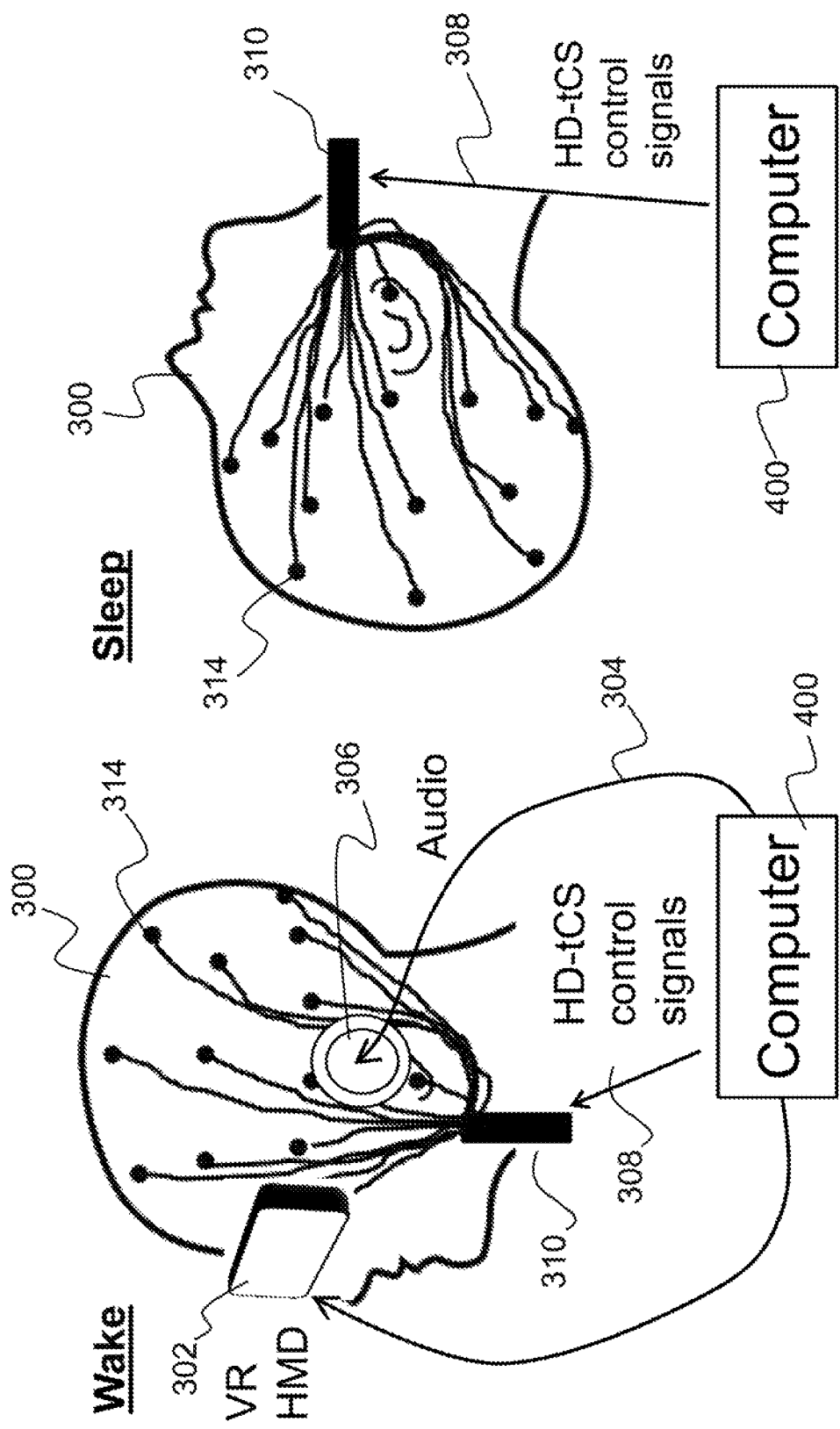
FIG. 3A is an illustration of a wake stage of the method for treatment of traumatic memories according to some embodiments of the present disclosure.
FIG. 3B is an illustration of a sleep stage of the method for treatment of traumatic memories according to some embodiments of the present disclosure.

FIGS. 3A and 3B depict the two stages of the invention described herein. FIG. 3A illustrates the wake stage, wherein the subject 300 relives the traumatic episode in the virtual world (created by three-dimensional (3D) images in a VR (virtual reality) head-mounted display 302 (e.g., a virtual reality system) and spatialized audio 304 over headphones 306). During the episode, a unique spatial pattern of high definition (HD) transcranial stimulation is applied (i.e. HD-tCS control signals 308). U.S. Non-Provisional Application Ser. No. 15/332,787, which is hereby incorporated by reference as though fully disclosed herein, described how such a pattern is determined. In short, the pattern is a set of currents, one for each stimulation electrode on the scalp, and this spatial pattern must be different from any other pattern associated with any other experience applied to this subject. During the sleep stage, as shown in FIG. 3B, when the computer 310 detects slow-wave oscillations in the HD-EEG data 312, the same pattern of stimulation is applied (i.e. HD-tCS control signals 308), thereby cueing a recall of the therapy session.

As shown in FIGS. 3A and 3B, the subject 300 wears a high-density array of electrical stimulators 314 HD-tCS (high-definition transcranial current stimulation) on his or her head. Additionally, the subject 300 wears a virtual reality head-mounted display 302 on the eyes ("VR HMD"), and spatialized audio 304 over headphones. A computer 308 projects a compelling virtual environment on the display 302, and the subject 300 should feel immersed and comfortable in the environment, as it is changed gradually to become very similar to the environment in which the subject experienced the traumatic episode. A therapist or a loved one can make the subject 300 feel comfortable and safe, for example, by holding a hand or putting a hand on a shoulder.

The painful memory is evoked by creating the situation in the virtual environment. The virtual reality simulator (see FIG. 4, element 400) notifies the HD-tCS controller (FIG. 4, element 310) the precise time when the painful memory is being simulated. From the time the memory is evoked, during the extent of the experience, a unique Spatial-Temporal Amplitude Modulated Pattern (STAMP) of weak current is applied to the scalp of the subject 300. The best result will be if the experience can be evoked suddenly and strongly, and for a short time span on the order of seconds or a minute, so that a strong mental impression can be associated with the STAMP. The strength of the experience may be determined by biometrics measurements from a sensor such as galvanic skin response relative to baseline readings from the subject taken before the session, or by subjective indications the subject can be asked to give, such as indicating a level of stress from 1 to 10 by holding up fingers.

Figure 4:
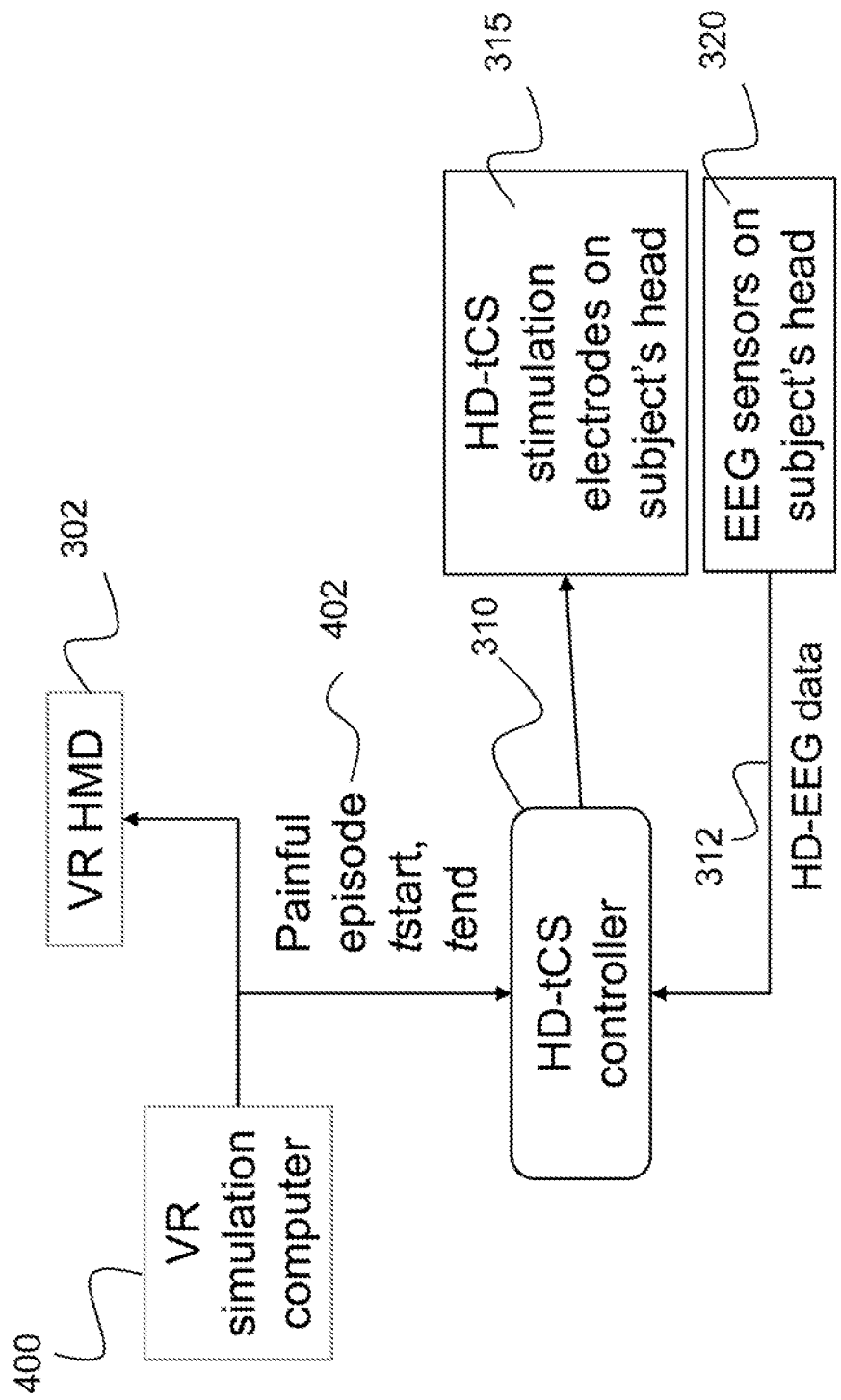
FIG. 4 is a flow diagram illustrating day operation of the system for treatment of traumatic memories according to some embodiments of the present disclosure.

FIG. 4 is a flow diagram depicting the day (or wake) operation stage of the present invention. As described above, a virtual world is created by a virtual reality simulator 400 and displayed via a virtual reality head-mounted display (VR HMD) 302. The virtual reality simulator 400 is a computer configured to render a 3D image of some environment that may be real or computer-generated, and display it on a stereoscopic display (such as a VR HMD), where the point-of-view of the display is controlled by location/direction/gyroscope sensors on the head and other parts of the body. The painful episode 402 (having a start and an end) is evoked by creating the situation in the virtual environment. For example, if a painful memory is associated with a room, the interior of a vehicle, or a particular outdoor location, the virtual environment may include images from photographs of that location. In some embodiments, the virtual environment may be a representation of that location created from software based on descriptions or images of the environment. Particular cues associated with the traumatic memory such as an item, people wearing camouflage, particular types of vehicles, implements, may be included in the virtual environment. In some embodiments, the situation created by the virtual environment may be new rather than based on a person's prior specific experiences. For example, the environment may include getting in various types of aircraft, or being on an elevated platform such as a balcony, porch, or cliff. Additional examples are provided below with respect to types of therapy sessions.

The virtual reality simulator 400 notifies the HD-tCS controller the precise time when the painful memory is being simulated. The computer 310 causes the tCS controller to apply a transcranial direct current stimulation (tDCS) stamp for the duration of the painful episode 402. tDCS is a form of neurostimulation that uses constant, low current delivered to electrodes arranged on the scalp. Thus, stimulation currents are held constant.

Figure 5:
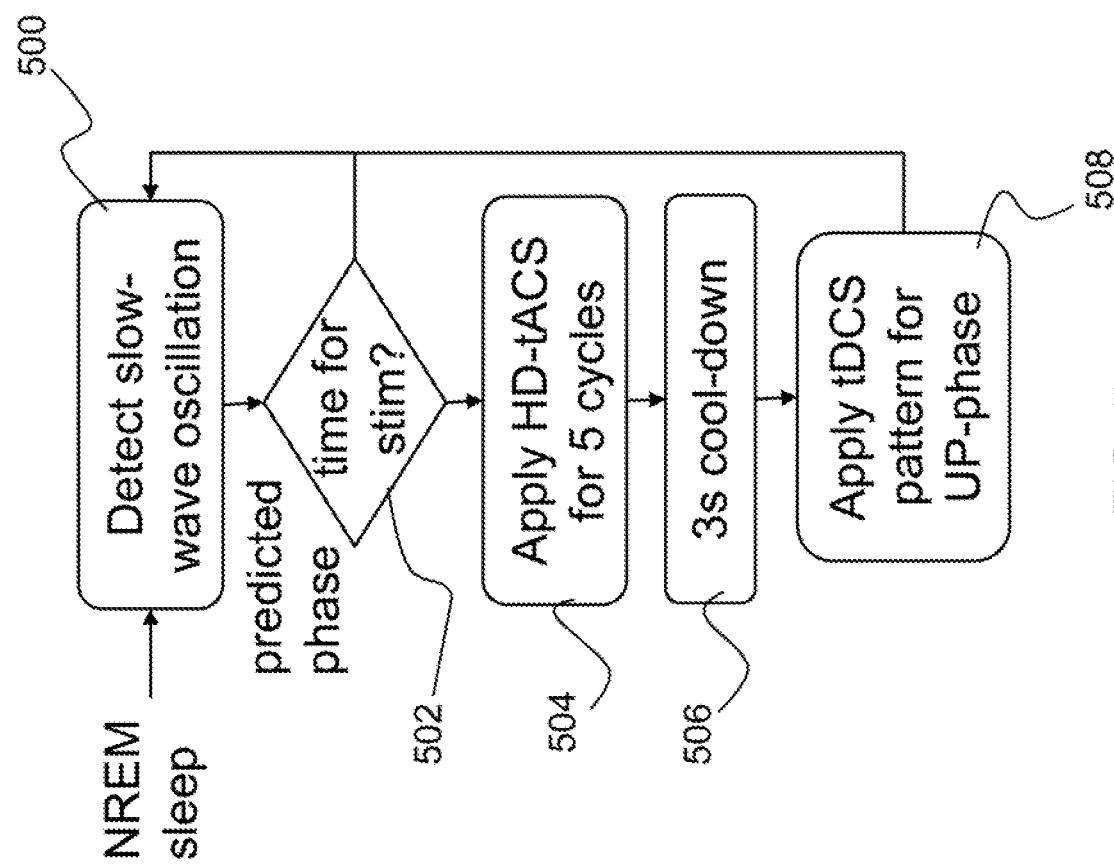
FIG. 5 is a flow diagram illustrating sleep operation of the system for treatment of traumatic memories according to some embodiments of the present disclosure.

FIG. 5 is a flow diagram illustrating a sleep operation (or stage), which is described in detail in U.S. Provisional Application No. 62/516,350, which is hereby incorporated by reference as though fully set forth herein. The technique employs a rolling mean of EEG channels and fits a 1 Hertz (Hz) oscillation to the previous second or so, and that fitted oscillation is the prediction for the next positive phase of the slow wave oscillation. Note that the actual phase of SWO constantly varies around 1 Hz so one has to constantly update prediction of the next UP phase. On the night after (or other suitable time) the therapy session described above for the day (or wake) operation stage, the subject 300 again wears the same high-density array of stimulators 314 on the head (FIG. 3B), this time including sensors, such as EEG (electro-encephalogram). The computer 308 monitors the EEG recording. When a period of slow-wave sleep is detected (element 500), such as a period when EEG oscillates at a frequency of 0.5-1 Hertz (Hz). The system then commands the HD-tCS array of stimulators to apply a short period (e.g., 5 cycles) of tACS (transcranial alternating current stimulation) to the prefrontal cortex (PFC) of the subject (element 504). tACS is a noninvasive means by which alternating electrical current applied through the skin and skull entrains in a frequency-specific fashion the neural oscillations of the underlying brain. tACS currents are time dependent and have a sinusoidal shape. Amplitude, frequency, and relative phases can be controlled across stimulation electrodes. This lengthens the period of slow-wave sleep and strengthens the amplitude of the slow-wave oscillation (SWO). The EEG can be analyzed after the stimulation, and the power of the SWO can be determined, as described in Literature Reference No. 6.

Then, after a short cool-down period (e.g., approximately 3 seconds) (element 506), the system causes the HD-tCS array to stimulate the STAMP montage for the duration of the positive half-cycle of the SWO (approximately 500 milliseconds (ms), called the UP-phase (element 508). The architecture of the slow-wave oscillation is well-known in the art, such as described in Literature Reference No. 7. These two stages (elements 504 and 506) lead to improved consolidation of the memory that was cued by the STAMP montage. Neuronal membrane potentials switch from a depolarized level during an UP-phase to a hyperpolarized level during a DOWN-phase. This shift in the membrane potential has been used to detect cortical UP/DOWN phases.

This two-stage process (FIGS. 3A-3B, 4, and 5) may be repeated to get the desired improvement in the subject's condition. A desired improvement would be a subjective judgement (e.g., a survey or questionnaire) of the PTSD sufferer who would report frequency and intensity of experiences of PTSD during the days and nights of treatment. When the subject feels that PTSD is no longer a debilitating condition, the subject's treatment could be stopped. All memories are consolidated during the SWO periods. The "time for stim?" box 502 in FIG. 5 becomes true when an UP-phase prediction is available and there is enough time to ramp up the stimulation (100 ms, depending on the tCS controller).

While the disclosure describes a specific embodiment employing transcranial direct current electrical stimulation (tDCS) and tACS, variations of the protocol are also possible. For instance, the intervention can include tACS alone or tDCS alone. Further, the tACS and/or tDCS can be delivered via implanted electrodes rather than transcranially. In addition, the intervention can include transcranial magnetic stimulation (TMS) or targeted memory reactivation (TMR) via auditory or olfactory stimulation. Moreover, in an alternative embodiment, exposure therapy in a session with a therapist talking though the traumatic experience may be used to replace the display of the virtual reality to the subject.

In summary, this disclosure describes a system to weaken a traumatic memory by using a unique, weak pattern of transcranially-applied electrical stimulation to tag a reactivation of the memory in a benign setting during a therapy session and, subsequently, to cue the benign association during sleep, thereby consolidating the benign association. During the therapy session in a virtual environment, the traumatic episode is recreated, and the STAMP pattern is applied while the stressful episode is being simulated. During positive phases of slow-wave oscillation (SWO) period of sleep, a period of tACS is applied, interleaved with the STAMP. The STAMP acts as a cue to reactivate the benign association. Some SWO cycles should be un-STAMPed to allow time for other memories to consolidate. The intensity of the traumatic episode can be increased from waking session to waking session, until the subject is relieved of the painful associations.

The therapy can be staged to present short, mild experiences during the first treatment periods, and gradually increase their intensity and duration. For example, to weaken a fear of heights, the first experience might be on a porch in a virtual environment, with no railing, only a meter or so off the ground. After enough sessions that the subject is comfortable, the porch can be raised by a meter or two at a time to present more challenging experiences. Likewise, for fear of flying, the first experiences might be just walking into an airplane and buckling the seat belt. Later, a takeoff can be added, and finally turbulence. It is easy to create very compelling experiences in such a virtual world.

Various fears may be addressed using this system, including fear of objects, animals, insects, sounds, sensations, experiences, smells, etc. For each case, the fear may be addressed by presenting the fear through virtual reality while making the experience more benign through the use of a controlled environment and/or the assistance of other persons. Fear of sensations and experiences may be simulated with props or controlled presentation of the feared experience. For example, fear of heat or cold may be addressed with gradually increasing application of the feared experience in small amounts to a subject while they are presented with the virtual environment and while transcranial direct current stimulation is applied to the subject.

The targeted transcranial neurostimulation system according to embodiments of the present disclosure will cure people of post-traumatic stress and irrational fears and rid them of disturbing memories without physical risk to the patient. It is reasonable and useful to fear traumatic events, but when such fears become crippling and debilitating, it is a problem. The invention described herein has goals similar to trauma-focused cognitive behavioral therapy techniques (e.g., Literature Reference No. 1) common in psychological treatment. The approach is to relive the trauma in a safe setting, guided by a skilled therapist, and learn a new association. However, unlike such techniques that require appointments with trained therapists for months or years of sessions, the system and method according to embodiment of this disclosure can accelerate treatment.

Unlike pharmacological intervention, the approach described herein has low physical risk and no pharmacological side effects, and will be more effective than behavioral therapies. Additionally, the approach will allow, for the first time, a targeted personalized closed-loop system for weakening the specific memories that are bothering the patient. Several commercial companies market high-definition transcranial stimulation products to which the invention described herein can be applied.

The advantages of the system and method according to embodiments of the present disclosure include the following. The therapeutic procedure is safe; it does not require drugs. The therapy can be added to standard psychological therapy techniques to greatly improve their effectiveness. The therapy is targeted; it is applied only during certain periods of sleep with the only side-effects being a more restful night's sleep (due to the AC protocol applied to lengthen the slow wave sleep stage), compared with a drug treatment whose effects can have unintended systemic chemical side-effects. As can be appreciated by one skilled in the art, the patient may sleep during the day and be awake during the night, so any reference to a "night's sleep" or "night operation" can be considered to be applicable to whenever the patient sleeps, day or night.

In addition, due to its ability to enhance the efficacy of therapy sessions, the system can significantly decrease the number of such sessions required. The desired end-result is subjective. The patient wants relief from debilitating PTSD experiences that may occur daily and can destroy a person's ability to hold down a job and/or to take care of their children. The resulting depression can lead to drinking or drugs to try to numb the emotions. There are well established assessment measures used to diagnose PTSD and to measure the effectiveness of therapy. There are a number of structured interviews and self-report questionnaires that may be used, and some are targeted at particular forms of PTSD (e.g., due to rape, battle, accidents). For instance, the Clinician-Administered PTSD Scale (CAPS) was created by the National Center for PTSD, and is one of the most widely used PTSD interviews (see Literature Reference No. 8). The first stage of transition would be a clinical system, for lab use where the disturbing memory needs to be artificially evoked. A second stage would be a home system that can be either self-initiated or works automatically. A final stage would be a portable personal therapy system that also can be operated by a naïve user with minimal supervision.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for treating fear and stress from traumatic memories, the system comprising:
    one or more processors and a non-transitory computer-readable medium having executable instructions encoded thereon such that when executed, the one or more processors perform operations of:
    during a wake stage, causing a virtual environment to be displayed via a virtual reality system in a benign setting;
    displaying a traumatic episode in the virtual environment via the virtual reality system, wherein the traumatic episode is created to include painful aspects of a traumatic memory;
    using a transcranial current stimulation (tCS) controller, applying a pattern of transcranial direct current stimulation (tDCS) while the traumatic episode is being displayed via the virtual reality system to associate the traumatic memory with the pattern of tDCS given in the benign setting; and
    during a sleep stage, when a period of slow-wave sleep is detected via electroencephalogram (EEG) recordings, causing the tCS controller to apply a transcranial alternating current stimulation (tACS) to the prefrontal cortex of the subject.

2. The system as set forth in claim 1, wherein the virtual environment is gradually altered to be similar to an environment in which the subject experienced the traumatic memory.

3. The system as set forth in claim 1, wherein the pattern of tDCS is a Spatial-Temporal Amplitude Modulated Pattern (STAMP).

4. The system as set forth in claim 1, wherein the duration of the tDCS application is varied based on the traumatic memory.

5. The system as set forth in claim 1, wherein the period of slow-wave sleep comprises a slow-wave oscillation, and wherein the one or more processors further perform an operation of, using the tCS controller, applying the pattern of tDCS for at least a portion of the slow-wave oscillation.

6. The system as set forth in claim 5, wherein the slow-wave oscillation comprises a plurality of UP phases, and wherein the one or more processors further perform an operation of, using the tCS controller, applying the pattern of tDCS to a percentage of the plurality of UP phases.

7. A computer implemented method for treating fear and stress from traumatic memories, the method comprising an act of:
    causing one or more processors to execute instructions encoded on a non-transitory computer-readable medium, such that upon execution, the one or more processors perform operations of:
    during a wake stage, causing a virtual environment to be displayed via a virtual reality system in a benign setting;
    displaying a traumatic episode in the virtual environment via the virtual reality system, wherein the traumatic episode is created to include painful aspects of a traumatic memory;
    using a transcranial current stimulation (tCS) controller, applying a pattern of transcranial direct current stimulation (tDCS) while the traumatic episode is being displayed via the virtual reality system to associate the traumatic memory with the pattern of tDCS given in the benign setting; and
    during a sleep stage, when a period of slow-wave sleep is detected via electroencephalogram (EEG) recordings, causing the tCS controller to apply a transcranial alternating current stimulation (tACS) to the prefrontal cortex of the subject.

8. The method as set forth in claim 7, wherein the virtual environment is gradually altered to be similar to an environment in which the subject experienced the traumatic memory.

9. The method as set forth in claim 7, wherein the pattern of tDCS is a Spatial-Temporal Amplitude Modulated Pattern (STAMP).

10. The method as set forth in claim 7, wherein the duration of the tDCS application is varied based on the traumatic memory.

11. The method as set forth in claim 7, wherein the period of slow-wave sleep comprises a slow-wave oscillation, and wherein the one or more processors further perform an operation of, using the tCS controller, applying the pattern of tDCS for at least a portion of the slow-wave oscillation.

12. The method as set forth in claim 11, wherein the slow-wave oscillation comprises a plurality of UP phases, and wherein the one or more processors further perform an operation of, using the tCS controller, applying the pattern of tDCS to a percentage of the plurality of UP phases.

13. A computer program product for treating fear and stress from traumatic memories, the computer program product comprising:
  computer-readable instructions stored on a non-transitory computer-readable medium that are executable by a computer having one or more processors for causing the processor to perform operations of:
    during a wake stage, causing a virtual environment to be displayed via a virtual reality system in a benign setting;
    displaying a traumatic episode in the virtual environment via the virtual reality system, wherein the traumatic episode is created to include painful aspects of a traumatic memory;
    using a transcranial current stimulation (tCS) controller, applying a pattern of transcranial direct current stimulation (tDCS) while the traumatic episode is being displayed via the virtual reality system to associate the traumatic memory with the pattern of tDCS given in the benign setting; and
  during a sleep stage, when a period of slow-wave sleep is detected via electroencephalogram (EEG) recordings, causing the tCS controller to apply a transcranial alternating current stimulation (tACS) to the prefrontal cortex of the subject.

14. The computer program product as set forth in claim 13, wherein the pattern of tDCS is a Spatial-Temporal Amplitude Modulated Pattern (STAMP).

15. The computer program product as set forth in claim 13, further comprising instructions for causing the one or more processors to cause the tCS controller to vary the duration of the tDCS application based on the traumatic memory.

16. The computer program product as set forth in claim 13, wherein the period of slow-wave sleep comprises a slow-wave oscillation, and wherein the computer program product further comprises instructions for causing the one or more processors to further perform an operation of, using the tCS controller, applying the pattern of tDCS for at least a portion of the slow-wave oscillation.

17. The computer program product as set forth in claim 16, wherein the slow-wave oscillation comprises a plurality of UP phases, and wherein the computer program product further comprises instructions for causing the one or more processors to further perform an operation of, using the tCS controller, applying the pattern of tDCS to a percentage of the plurality of UP phases.

18. The system as set forth in claim 1, wherein the virtual environment is altered in a series of sessions to gradually increase the level of discomfort of a subject.

19. The system as set forth in claim 1, wherein following a duration of application of the tACS to the prefrontal cortex of the subject, a duration of no stimulation occurs, wherein the duration of no stimulation is shorter than the duration of application of the tACS, and wherein following the duration of no stimulation, the one or more processors further perform an operation of causing the tCS controller to apply the pattern of tDCS to the subject to weaken the traumatic memory.

20. The method as set forth in claim 7, wherein the virtual environment is altered in a series of sessions to gradually increase the level of discomfort of a subject.

21. The method as set forth in claim 7, wherein following a duration of application of the tACS to the prefrontal cortex of the subject, a duration of no stimulation occurs, wherein the duration of no stimulation is shorter than the duration of application of the tACS, and wherein following the duration of no stimulation, the one or more processors further perform an operation of causing the tCS controller to apply the pattern of tDCS to the subject to weaken the traumatic memory.

* * * * *